(12) United States Patent
Friend et al.

(10) Patent No.: US 8,998,483 B2
(45) Date of Patent: Apr. 7, 2015

(54) CONCENTRATION AND DISPERSION OF SMALL PARTICLES IN SMALL FLUID VOLUMES USING ACOUSTIC ENERGY

(75) Inventors: James Robert Friend, Brighton (AU); Leslie Yu-Ming Yeo, Glen Iris (AU)

(73) Assignee: Royal Melbourne Institute Technology, Melbourne, Victoria (AU)

( * ) Notice: Subject to any disclaimer, the term of this patent is extended or adjusted under 35 U.S.C. 154(b) by 1254 days.

(21) Appl. No.: 12/298,804

(22) PCT Filed: May 2, 2007

(86) PCT No.: PCT/AU2007/000576
§ 371 (c)(1),
(2), (4) Date: May 1, 2009

(87) PCT Pub. No.: WO2007/128046
PCT Pub. Date: Nov. 15, 2007

(65) Prior Publication Data
US 2009/0206171 A1  Aug. 20, 2009

(30) Foreign Application Priority Data
May 2, 2006  (AU) .............................. 2006902258

(51) Int. Cl.
*B01F 11/02* (2006.01)
*B01F 13/00* (2006.01)
(Continued)

(52) U.S. Cl.
CPC ............. *B01F 11/02* (2013.01); *B01F 13/0071* (2013.01); *B01L 3/502761* (2013.01);
(Continued)

(58) Field of Classification Search
CPC ... B01F 13/0071; B01F 11/02; G01N 29/222; G01N 2035/1046; B01L 3/502792; B01L 3/502761; B01L 2200/0668; B01L 2400/0436
USPC .................... 366/127, 348, 341; 204/643
See application file for complete search history.

(56) References Cited

U.S. PATENT DOCUMENTS 6,669,454 B2   12/2003  Lal et al. ..................... 417/410.2
6,673,225 B1 *  1/2004  Arnold ........................... 204/547
(Continued)

FOREIGN PATENT DOCUMENTS

DE        10325307      7/2004
JP      2003/071277     3/2003
(Continued)

OTHER PUBLICATIONS

Tseng et al, 'Active micro-mixers using surface acoustic waves on Y-cut 128 LiNbO3', 2006, Journal of Micromechanics and Microengineering, pp. 539-548.*
(Continued)

*Primary Examiner* — Yogendra Gupta
*Assistant Examiner* — Emmanuel S Luk
(74) *Attorney, Agent, or Firm* — Baker & Hostetler LLP

(57) ABSTRACT

A method of manipulating particles suspended within a fluid droplet using a microfluidic system including a piezo-electric substrate (1) and a wave generation means (3) for generating a wave within the piezoelectric substrate (1), and a working surface (2) through which the wave can be distributed and upon which fluid droplets (9) can be located, the method including locating one or more droplets of fluid on the working surface (2), varying the power applied to the wave generation means (3) or varying the distribution of the wave across the working surface (2), such that particles (1 1) suspended within the fluid droplet (9) are either dispersed within the droplet or concentrated in an area within the droplet in dependence on the power or wave distribution applied by the wave generation means (3) to the piezoelectric substrate (1), or to facilitate rotation of the fluid within said fluid droplets (9) located jn the path of the wave.

2 Claims, 2 Drawing Sheets

(51) Int. Cl.
  *B01L 3/00* (2006.01)
  *G01N 29/22* (2006.01)
  *G01N 35/10* (2006.01)

(52) U.S. Cl.
  CPC ........ B01L3/502792 (2013.01); G01N 29/222 (2013.01); *B01L 2200/0668* (2013.01); *B01L 2400/0436* (2013.01); *G01N 2035/1046* (2013.01)

(56) References Cited

U.S. PATENT DOCUMENTS

| | | | |
|---|---|---|---|
| 6,682,214 B1* | 1/2004 | Vivek et al. | 366/108 |
| 6,777,245 B2* | 8/2004 | Wixforth | 436/180 |
| 7,942,568 B1* | 5/2011 | Branch et al. | 366/127 |
| 7,981,368 B2* | 7/2011 | Laugharn et al. | 422/128 |
| 8,038,337 B2* | 10/2011 | Rathgeber et al. | 366/115 |
| 8,147,668 B2* | 4/2012 | Pollack et al. | 204/547 |
| 2004/0200724 A1* | 10/2004 | Fujii et al. | 204/601 |
| 2006/0024206 A1 | 2/2006 | Sinha et al. | 422/100 |

FOREIGN PATENT DOCUMENTS

| | | | | |
|---|---|---|---|---|
| JP | 2003-535349 T | 11/2003 | | |
| JP | 2004-195340 A | 7/2004 | | |
| JP | 2004-534633 T | 11/2004 | | |
| JP | 2005-504623 T | 2/2005 | | |
| JP | 2005-254112 A | 9/2005 | | |
| JP | 2006/519685 | 8/2006 | | |
| WO | WO2004/076046 | * | 9/2004 | ............ B01F 13/00 |
| WO | WO 2006/027602 | 3/2006 | | |

OTHER PUBLICATIONS

Luong et al, 'High-throughput micromixers based on acoustic streaming induced by surface acoustic wave', 2011, Micorfluid Nanofluid, pp. 619-625.*

Sritharan, et al., "Acoustic Mixing at Low Reynold's Numbers", *Applied Physics Letters 88*, Feb. 2, 2006.

Wixforth, A., "Acoustically Driven Planar Microfluidics", *Superlattices and Microstructures 33* (2003), pp. 389-396.

Zhu, X., et al., "Microfluidic Motion Generation with Loosely-Focused Acoustic Waves", *IEEE Transducers 1997 International Conference on Solid-State Sensors and Actuators*, Chicago, Jun. 16-19, 1997, pp. 837-838.

Translation of Japanese Patent Application No. 2009-508045: Notice of Reasons for Rejection dated Aug. 30, 2011, 4 pages.

* cited by examiner

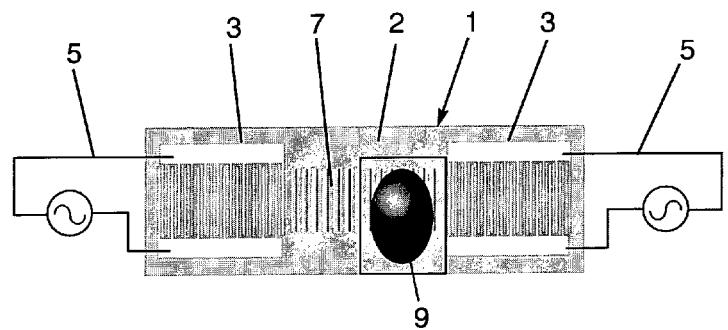
Figure 1
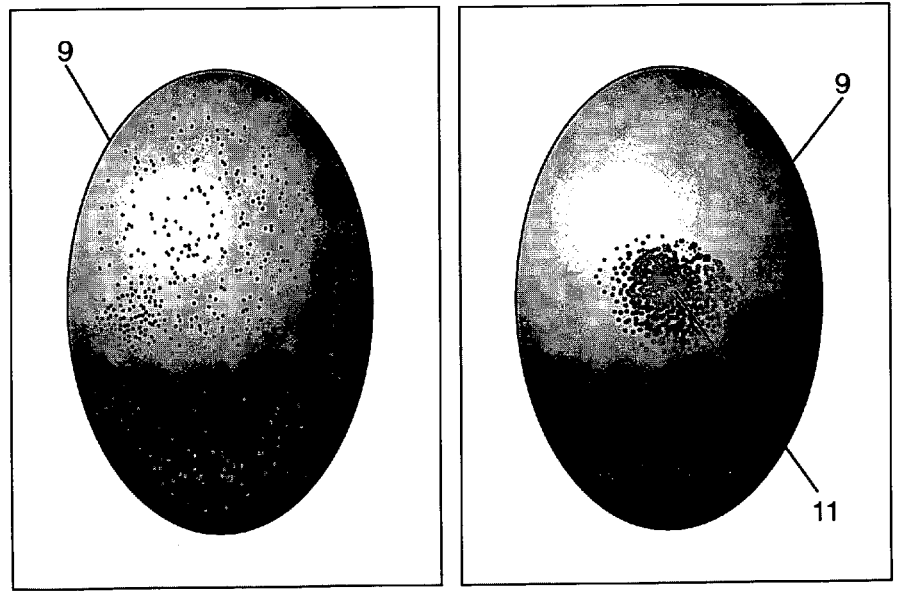
Figure 2                    Figure 3

CONCENTRATION AND DISPERSION OF SMALL PARTICLES IN SMALL FLUID VOLUMES USING ACOUSTIC ENERGY

CROSS-REFERENCE TO RELATED APPLICATIONS

This application is the National Stage of International Application No. PCT/AU2007/000576, filed May 2, 2007, which claims priority to Australian Application No. 2006902258 filed May 2, 2006, the disclosures of which are incorporated herein by reference in their entireties.

The present invention generally relates to microfluidic systems, and is in particular directed to the concentration and dispersion of small particles in small fluid volumes using acoustic energy in such systems.

The ongoing development and research in microfluidic processes and systems is driven by the many benefits that can be achieved by conducting processes on fluids at a microscale. In particular, in fluid analysis applications, only small volumes of fluid are required. Also, only small quantities of the associated reagents and analytes are required leading to cost savings. In addition, there are lower power requirements to operating such systems. Furthermore, the potential of mass production of such systems using integrated circuit fabrication methods make them attractive as relatively low cost, portable and disposable diagnostic devices. Greater control can be achieved in the mixing of fluids as the mixing is primarily due to diffusion between the fluids. These systems can also be used in biomedical applications where biological materials such as erythrocytes or bacteria need to be concentrated within the fluid with little to no damage of that material. Many other existing and potential applications are also envisaged for such microfluidic systems.

A simple microfluidic system would typically include a substrate formed of material such as silicon, glass, polymeric film or thermoplastic in which is etched, laser cut or moulded microfluidic channels. Such channels would typically have at least one dimension of less than 1 mm. A cover may also be provided over the channels to enclose them. A syringe or a microelectromechanical system (MEMS) may then be used to transport fluids, and any associated reagents or analytes through these channels.

More sophisticated microfluidic systems utilize piezoelectric actuators which are actuated for vibration using electrical excitation. In one such system, capillaries are mounted on or mechanically coupled to such an actuator to thereby allow for ultrasonic vibration of the capillary. This has a particular application in the concentration of biological material within pressure nodes located within the acoustic standing wave generated by the vibration of the capillary. The major disadvantage of such capillary based systems is that it is difficult to subsequently remove the fluid and the concentrated material from the capillaries.

All the above described applications use a continuous flow of fluid through channels or capillaries. It is also possible to conduct microfluidic processes on individual droplets of fluid. These droplets may be applied directly to the surface of a piezoelectric substrate and may then be directly exposed to vibrations generated within the substrate using radio frequency (RF) pulsed excitation. One such system uses a piezoelectric substrate upon which the surface of the piezoelectric substrate is located at least one interdigital electrode. Application of a RF input to the electrodes generates within the piezoelectric substrate surface a surface acoustic wave (SAW), also known as a "Rayleigh" wave. The SAW excitation of the substrate surface acts to displace or manipulate one or more fluid droplets located on that surface.

It would be advantageous to be able to provide a microfluidic system and a method of using such systems which overcomes the above-noted disadvantage in the collection of concentrated particles.

Any discussion of documents, systems, acts or knowledge in this specification is included to explain the context of the invention. It should not be taken as an admission that any of the material formed part of the prior art base or the common general knowledge in the relevant art in or any other country on or before the priority date of the claims herein.

According to one aspect of the present invention, there is provided a method of manipulating particles suspended within a fluid droplet using a microfluidic system including a piezoelectric substrate and a wave generation means for generating a wave within the piezoelectric substrate, and a working surface through which the wave can be distributed and upon which fluid droplets can be located, the method including locating one or more droplets of fluid on the working surface, varying the power applied to the wave generation means, such that particles suspended within the fluid droplet are either dispersed within the droplet or concentrated in an area within the droplet in dependence on the power applied by the wave generation means to the piezoelectric substrate.

The Applicant has found that the particles generally concentrate into a specific area, typically the centre, of the droplet when a modest amount of power is applied to the piezoelectric substrate, less than 5% of the maximum continuous power that may be put into the SAW device. The particles however disperse into the droplet when even less power is applied to the piezoelectric substrate, over a range between 0.5 and 2% of the maximum continuous power that may be put into the SAW device. The actual power appropriate for the two cases is dependent on the droplet's fluid properties and volume, its placement on the working surface, and the particulate concentration, shape, and composition. This is in part because the wave in the working surface acts to induce a rotation of the fluid within the fluid droplet leading to the concentration or distribution of the particles within the fluid droplet. The rotation is at least in part as a result of the viscous absorption of acoustic energy in the droplet.

The wave generation means may generate a surface acoustic wave (SAW) in the surface of the piezoelectric substrate. It is however also envisaged that other forms of waves could be used in this system to deliver acoustic energy to the secondary substrate including bulk acoustic waves (BAW), surface-skimming bulk waves (SSBW) and shear surface acoustic waves (SH-SAW).

According to another aspect of the present invention, there is provided a method of manipulating particles suspended within a fluid droplet using a microfluidic system including a piezoelectric substrate and a wave generation means for generating a wave within the piezoelectric substrate, and a working surface through which the wave can be distributed and upon which fluid droplets can be located, the method including locating one or more droplets of fluid on the working surface, varying the distribution of the generated wave across the working surface, such that particles suspended within the fluid droplet are either dispersed within the droplet or concentrated in an area within the droplet in dependence on the distribution of the generated wave across the working surface.

The wave generation means may generate a surface acoustic wave (SAW) in the surface of the piezoelectric substrate and may include at least one interdigital electrode deposited on the piezoelectric substrate, and electrical supply mean for applying an RF input into the electrode.

Varying the distribution of the generated wave across the width of the working surface facilitates rotation of the fluid within the fluid droplet when located in the path of the wave. Various means may be provided to allow for the variation in the distribution of the wave as will subsequently be discussed.

The applicants have demonstrated the rapid concentration of particles in a sessile droplet in 2-20 s by inducing azimuthal bulk liquid recirculation acoustic streaming within the droplet with the use of SAW radiation on the substrate upon which the droplet is placed. A key to inducing azimuthal recirculation is an asymmetry in the SAW radiation across the width of the droplet and preferably transverse to the SAW propagation direction. This results from varying the distribution of the SAW across the working surface. Once a sufficient initial local particle concentration is attained along the azimuthal streamline generated by acoustic streaming, shear-induced migration dominates, giving rise to an inward radial force that concentrates the particles at the centre of the droplet. Redispersion of the particle aggregate can also be achieved by increasing the input power such that the bulk internal convection dominates over shear-induced migration such that the outwardly directed centripetal acceleration overcomes the shear-induced diffusion process. The particle concentration process according to the present invention is faster than currently available particle concentration mechanisms due to the large convective velocities achieved using the SAW device. Moreover, the concentration process is also efficient, concentrating the particles into an aggregate about 10% of the size of the droplet. It was also verified that bioparticles concentrated using this process were not damaged by the SAW radiation. These findings indicate that the limitations of current biosensors can be resolved with the use of the proposed SAW concentration device. The analyte detection sensitivity can thus be increased due to the particle concentration process allowing a wider range of sensor technologies to be used. Moreover, the rapid concentration process reduces the diffusion limitation to the molecular binding couple-matching process as well as the total concentration and detection time. It is thus believed that these advantages will economically improve biosensor technology by using these SAW techniques.

According to a further aspect of the present invention there is provided a microfluidic system including:

an elongate piezoelectric substrate having opposing ends thereof;

a wave generation means for generating a wave in the piezoelectric substrate;

a working surface through which the generated wave can be distributed, and upon which at least one fluid droplet within which is suspended particles can be located; and means for varying the distribution of the wave across the width of the working surface to thereby facilitate rotation of the fluid within a said droplet of fluid located in the path of the wave.

The facilitation of the fluid rotation results in either greater dispersion of or concentration of the particles within the fluid droplet as previously discussed.

The wave may be in the form of a surface acoustic wave (SAW), although the use of other forms of waves for delivering acoustic energy to the piezoelectric substrate is also envisaged as mentioned previously.

The wave generation means may include at least one interdigital electrode deposited on the piezoelectric substrate, and electrical supply means for applying an radio frequency (RF) input into the electrode. It is however also envisaged that other types of transducers could be used to generate the SAW wave or other waves in the piezoelectric substrate.

The means for varying the distribution of the SAW wave may in one possible arrangement include an oblique reflection surface provided at the end of the piezoelectric substrate opposing the interdigital electrode. The SAW wave is therefore reflected at an oblique angle from the reflection surface resulting in a variation in the distribution of the SAW wave across the width of the working surface.

The means for varying the distribution of the SAW wave may in another possible embodiment include damping material located in a position offset relative to the general path of the SAW wave at the end of the piezoelectric substrate opposing the interdigital electrode. The offset position of the damping material also acts to influence the reflection of the SAW wave resulting in the variation in the SAW wave distribution across the width of the working surface.

Other means to effect a distribution of the SAW wave across the width of the working surface are also envisaged. The interdigital electrodes include a plurality of interlaced fingers, and the thickness or width of each finger may vary along the electrode in the SAW propagation direction. Alternatively, the electrode itself may vary in width continuously or in discrete steps along the SAW propagation direction.

The piezoelectric substrate itself may be conventionally formed from Lithium Niobate ($LiNbO_3$). Other types of piezoelectric material may also be used as it is possible to induce waves in polycrystalline piezoelectric material including barium titanate ($BiTaO_3$), lead zirconium titanate (PZT or $PbZrO_3$, often with dopants to improve performance), zinc oxide (ZnO), aluminum nitride (AlN), and single crystal materials like lithium tantalate (LiTaO3), quartz, langasite ($La_3Ga_5SiO_{14}$), and gallium orthophosphate (GaPO4).

The working surface may be the surface of the piezoelectric substrate. However, if the fluid droplet is caustic, this can damage the surface of the piezoelectric substrate. Therefore, according to another arrangement, a coating may be applied to the piezoelectric substrate to protect its surface and provide the working surface thereof. A typical approach is to use a thin coating of silicon dioxide, although the use of other coating materials is also envisaged. The use of coatings could however potentially lead to absorption of the SAW wave generated in the piezoelectric substrate. Therefore, in a co-pending application of the Applicant, the working surface may be provided by a rigid secondary substrate coupled to the surface of the piezoelectric substrate, preferably by a fluid coupling layer. This arrangement facilitates the distribution of the SAW wave to the working surface of the secondary substrate.

The microfluidic system according to the present invention can allow for the concentration of particles on the working surface facilitating the collection of those particles. This arrangement has advantages over capillary based systems where it is difficult to collect the particles concentrated within the capillaries.

It will be convenient to further describe the invention with respect to the accompanying drawings which illustrate preferred embodiments of the microfluidic system according to the present invention. Other arrangements of the invention are possible, and consequently, the particularity of the accompanying drawings is not to be understood as superseding the generality of the preceding description of the invention.

IN THE DRAWINGS:

FIG. 1 is a plan view of a preferred embodiment of a microfluidic system according to the present invention;

FIG. 2 is a plan view of a fluid droplet showing the distribution of particles within the droplet prior to the application of the present invention;

FIG. 3 shows the concentration of particles within the fluid droplet of FIG. 2 following application of the present invention;

Figure 4:
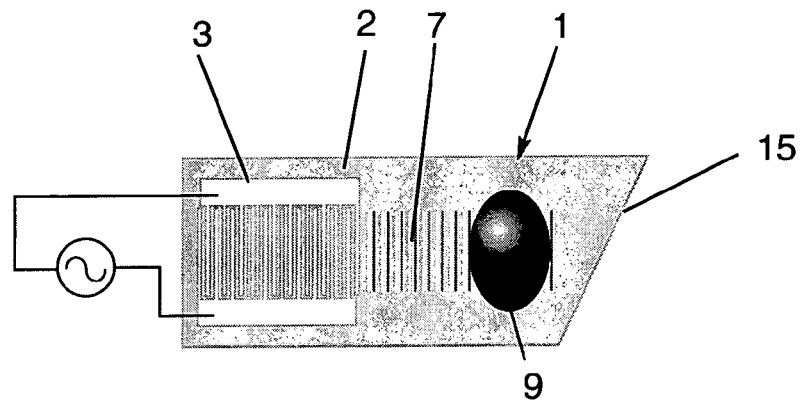
FIG. 4 is a plan view of another preferred embodiment of the present invention.
Figure 5:
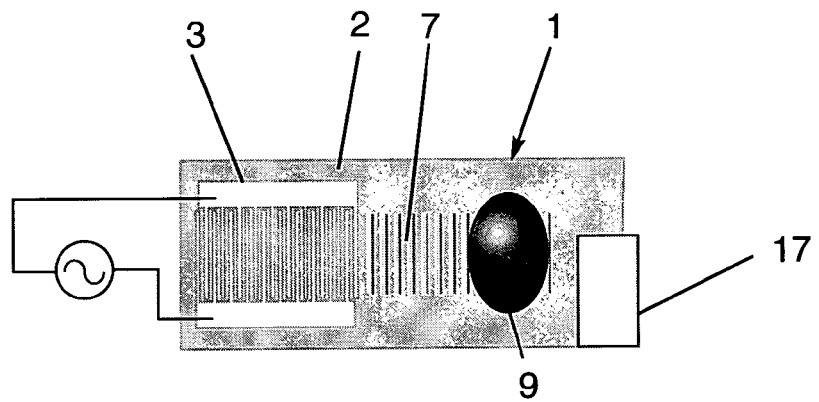
FIG. 5 is a plan view of a further preferred embodiment according to the present invention.

Referring initially to FIG. 1, the microfluidic system according to the present invention includes an elongate piezoelectric substrate 1. Located at opposing ends of that substrate 1 are interdigital electrodes 3, each electrode receiving a pulsed excitation through a radio frequency (RF) input 5. The pulse excitation of the interdigital electrodes 3 results in a surface acoustic wave (SAW) 7 being generated in the upper surface 2 of the piezoelectric substrate 1. Depending on the configuration of the interdigital electrodes 3 and the piezoelectric substrate 1, the SAW wave 7 may be either a standing or a travelling wave generated within the upper surface 2. The frequency of the pulse excitation can be typically in the order of between 10 to 1000 MHz, although this frequency can vary depending on the resonance frequency of the interdigital electrodes 3 and the physical properties of the piezoelectric substrate 1.

The applicant has found that the application of acoustic energy to a fluid droplet 9 placed on the upper surface 2 or a working surface coupled to this upper surface 2, when exposed to the generated SAW wave 7 will result in dispersion or concentration of small particles within the fluid droplet 9. This is best shown in FIGS. 2 and 3 which shows the effect of the transmission of acoustic energy to the droplet 9, with FIG. 3 showing the particles being concentrated in a mass 11 towards the centre of the fluid droplet 9.

The applicant has found that the manipulation of the particles within the fluid droplet 9 depends on the degree of power provided to the interdigital electrodes 3 and thereby, the acoustic energy absorbed by the fluid droplet 9. At relatively low power, the particles tend to disperse more within the fluid droplet 9. At a sufficiently high power however, the particles can concentrate into an area within the fluid droplet 9.

The displacement of the particles within the fluid droplet 9 is facilitated by the rotation of the fluid in the fluid droplet 9. This rotation is at least in part as a result of the viscous absorption of the acoustic energy in the droplet 9. The rotation of fluid within the fluid droplet 9 can however be encouraged if the generated SAW wave 7 is not evenly distributed to the fluid droplet 9. This could be achieved in the possible arrangement shown in FIG. 1 by locating the fluid droplet 9 in an offset position relative to the general path of propagation of the SAW wave 7 so that only a part of the droplet 9 is directly exposed to the main wave front of the SAW wave 7.

Alternatively, the microfluidic system according to the present invention may be provided with means to allow for varying the distribution of the SAW wave 7 across the width of the upper surface 2 of the piezoelectric substrate 1 thereby facilitating rotation of the fluid within the fluid droplet when located in the path of the SAW wave.

FIG. 4 shows another preferred embodiment which differs from the arrangement shown in FIG. 1 in that only a single interdigital electrode 3 is provided at one end of the piezoelectric substrate 1, the other end of that substrate 1 being configured to provide an oblique reflection face 15 which is aligned at an angle to the general direction of propagation of the SAW wave 7 generated by the interdigital electrode 3. The SAW wave 7 will bounce off the oblique reflection face 15 at an angle to its original direction thereby resulting in a variation in the distribution of the SAW wave across the upper surface 2 of the piezoelectric substrate 1. The fluid droplet 9 located on the upper surface 2 will then be exposed to asymmetries in the SAW wave which will help to induce rotation of fluid within that droplet.

FIG. 5 shows another preferred embodiment of a microfluidic system according to the present invention which, as above, includes a piezoelectric substrate 1 having an interdigital electrode 3 located at one end thereof for generating an SAW wave 7. At the other end of the piezoelectric substrate 1 is provided a piece of damping material 17 which is located in an offset position relative to the general direction of the propagation of the SAW wave 7. This damping material 17 acts to dampen the intensity of the reflection of a portion of the reflected SAW wave 7 thereby resulting in the variation and distribution of the SAW wave within the upper surface 2 of the piezoelectric substrate 1. This arrangement also acts to encourage rotation of fluid within a fluid droplet 9 located on the upper surface 2 between the interdigital electrode 3 and the damping material 17.

Another possible means to effect a spatial variation of the SAW wave 7 across the width of the droplet would require the interdigital electrode 3 to have a configuration that changes with respect to the width, continuously or in discrete steps, either in the thickness of the metal film that forms the electrode, the width of the individual fingers that form the electrode, or the width of the entire electrode along the SAW propagation direction. In the last arrangement, a change in the excitation frequency of the piezoelectric substrate 1 would cause a different section of the electrode 3 to drive a surface acoustic wave along the substrate 1.

Modifications and variations as would be deemed obvious to the person skilled in the art are included within the ambit of the present invention as claimed in the appended claims.

The invention claimed is:

1. A method of manipulating particles suspended within a fluid droplet using a microfluidic system comprising a piezoelectric substrate and at least one interdigital electrode deposited on the piezoelectric substrate for generating a surface acoustic wave within the piezoelectric substrate, and a working surface through which the surface acoustic wave can be distributed and upon which fluid droplets can be located, the method comprising locating one or more droplets of fluid on the working surface, varying the distribution of the generated surface acoustic wave across the working surface, such that particles suspended within the fluid droplet are either dispersed within the droplet or concentrated in an area within the droplet as a result of azimuthal recirculation induced within the droplet in dependence on the distribution of the generated wave across the width of the working surface.

2. A method according to claim 1 further comprising applying an RF input into the electrode.

* * * * *